(12) United States Patent
Yoshinaka et al.

(10) Patent No.: US 8,217,127 B2
(45) Date of Patent: Jul. 10, 2012

(54) (METH)ACRYLIC ACID/ALKYL (METH)ACRYLATE ESTER COPOLYMER AND COSMETIC PREPARATION CONTAINING THE SAME

(75) Inventors: Masatoyo Yoshinaka, Himeji (JP); Yuichiro Morimitsu, Himeji (JP); Shinji Kobayashi, Kako-gun (JP); Masaki Kosugi, Kita-ku (JP)

(73) Assignee: Sumitomo Seika Chemicals Co., Ltd., Kako-gun (JP)

( * ) Notice: Subject to any disclaimer, the term of this patent is extended or adjusted under 35 U.S.C. 154(b) by 0 days.

(21) Appl. No.: 12/809,854

(22) PCT Filed: Dec. 19, 2008

(86) PCT No.: PCT/JP2008/073156
§ 371 (c)(1),
(2), (4) Date: Jun. 21, 2010

(87) PCT Pub. No.: WO2009/084469
PCT Pub. Date: Jul. 9, 2009

(65) Prior Publication Data
US 2010/0267845 A1    Oct. 21, 2010

(30) Foreign Application Priority Data
Dec. 28, 2007 (JP) .................... 2007-340497

(51) Int. Cl.
*C08F 20/10* (2006.01)
*C08F 112/02* (2006.01)
*A61K 47/32* (2006.01)

(52) U.S. Cl. .................. 526/318.4; 526/319; 514/772.6

(58) Field of Classification Search .............. 526/318.4, 526/319; 514/772.6
See application file for complete search history.

(56) References Cited

U.S. PATENT DOCUMENTS

| 3,915,921 A | * | 10/1975 | Schlatzer, Jr. ............ 526/238.23 |
| 3,940,351 A | | 2/1976 | Schlatzer, Jr. |
| 4,509,949 A | * | 4/1985 | Huang et al. ..................... 8/558 |
| 5,004,598 A | | 4/1991 | Lochhead et al. |
| 5,736,125 A | | 4/1998 | Morawsky et al. |
| 6,569,409 B1 | | 5/2003 | Hansenne et al. |
| 2001/0018484 A1 | | 8/2001 | Bitler et al. |
| 2002/0006419 A1 | | 1/2002 | Lorant |
| 2005/0271611 A1 | | 12/2005 | Yoshida et al. |
| 2007/0225522 A1 | * | 9/2007 | Kobayashi et al. ........... 562/525 |

FOREIGN PATENT DOCUMENTS

| JP | 51-6190 | | 1/1976 |
| JP | 59-232107 | A | 12/1984 |
| JP | 4-39312 | A | 2/1992 |
| JP | 10-53625 | A | 2/1998 |
| JP | 2000-119131 | A | 4/2000 |
| JP | 2000-507273 | A | 6/2000 |
| JP | 2002-520263 | A | 7/2002 |
| JP | 2003-509539 | A | 3/2003 |
| JP | 2005-350368 | A | 12/2005 |

* cited by examiner

*Primary Examiner* — Michael M Bernshteyn
(74) *Attorney, Agent, or Firm* — Oblon, Spivak, McClelland, Maier & Neustadt, L.L.P.

(57) ABSTRACT

A (meth)acrylic acid/alkyl (meth)acrylate ester copolymer containing:
  95.42 to 97.48% by mass of (meth)acrylic acid;
  2.43 to 4.30% by mass of an alkyl (meth)acrylate ester, and
  0.08 to 0.30% by mass of a compound having two or more ethylenically unsaturated groups.
Use in cosmetics.

20 Claims, No Drawings

(METH)ACRYLIC ACID/ALKYL (METH)ACRYLATE ESTER COPOLYMER AND COSMETIC PREPARATION CONTAINING THE SAME

This application is a 371 of PCT/JP2008/073156, filed Dec. 19, 2008.

TECHNICAL FIELD

The present invention relates to a (meth)acrylic acid/alkyl (meth)acrylate ester copolymer. More specifically, the present invention relates to a (meth)acrylic acid/alkyl (meth)acrylate ester copolymer which can be suitably used as an aqueous thickener for cosmetics or the like, and cosmetics blended with the copolymer.

BACKGROUND ART

Various copolymers have been known as (meth)acrylic acid/alkyl (meth)acrylate ester copolymers, usable in an aqueous thickener for cosmetics or the like, a moisture-retaining agent for poultice or the like, a suspension stabilizing agent for an emulsifying agent, a suspension, or the like. For example, a copolymer prepared by reacting a specified amount of an olefinic unsaturated carboxylic acid monomer and a specified amount of an alkyl (meth)acrylate ester, of which alkyl group has 10 to 30 carbon atoms (see Patent Publication 1); a copolymer prepared by reacting a specified amount of an olefinic unsaturated carboxylic acid monomer, a specified amount of an alkyl (meth)acrylate ester, of which alkyl group has 10 to 30 carbon atoms, and a crosslinking agent (see Patent Publication 2); a copolymer prepared by reacting an olefinic unsaturated carboxylic acid monomer and an alkyl (meth)acrylate ester, of which alkyl group has 8 to 30 carbon atoms (see Patent Publication 3); and the like have been known. These (meth)acrylic acid/alkyl (meth)acrylate ester copolymers can be used in each of the applications mentioned above by usually dissolving the copolymer in water or the like, and thereafter neutralizing the solution with an alkali to prepare a neutral viscous aqueous solution having a concentration of about 0.1 to about 1% by mass.

However, in a case where an electrolyte is co-present in various raw materials and an additive constituting the manufactured articles, there are some disadvantages that a neutral viscous aqueous solution thereof has a lowered viscosity or a greater temperature dependence even at its relatively low concentration, the stability of the manufactured articles containing these aqueous solutions undesirably worsens with time, or the like. Further, there are some disadvantages that the aqueous solution also has lowered transmittance, and that a part of the copolymer is precipitated.

In particular, in recent years, in the field of cosmetics, in order to achieve differentiations among the commercial products, cosmetics having such properties as those including an active ingredient such as an electrolyte, or a mineral component in a high content, those having excellent external appearance with high transparency, and those giving a feel without stickiness are being remarked. In addition, a proposal of a thickener having properties that can expect improvements in production efficiency in various production steps has been desired, from the viewpoint of the request of reduction in production costs.

Patent Publication 1: Japanese Patent Laid-Open No. Sho 51-6190
Patent Publication 2: Japanese Patent Laid-Open No. Sho 59-232107
Patent Publication 3: U.S. Pat. No. 5,004,598

DISCLOSURE OF INVENTION

Problems to be Solved by the Invention

An object of the present invention is to provide a (meth)acrylic acid/alkyl (meth)acrylate ester copolymer capable of forming a neutral viscous aqueous solution having a stable viscosity independent on its concentration or temperature, even in the presence of an electrolyte having a relatively high concentration, and cosmetics blended with the copolymer.

Means to Solve the Problems

The present invention is concerned with a (meth)acrylic acid/alkyl (meth)acrylate ester copolymer as shown hereinbelow:

Item 1. A (meth)acrylic acid/alkyl (meth)acrylate ester copolymer containing constituents of:
95.42 to 97.48% by mass of (meth)acrylic acid,
2.43 to 4.30% by mass of an alkyl (meth)acrylate ester of which alkyl group has 18 to 24 carbon atoms, and
0.08 to 0.30% by mass of a compound having two or more ethylenically unsaturated groups,
wherein the (meth)acrylic acid/alkyl (meth)acrylate ester copolymer has the following properties:
1) a viscosity of a neutral viscous aqueous solution containing 1% by mass of the (meth)acrylic acid/alkyl (meth)acrylate ester copolymer and 1% by mass of sodium chloride being 40000 mPa·s or more at 25° C., and a ratio of a viscosity of the neutral viscous aqueous solution at 25° C. to a viscosity of the neutral viscous aqueous solution at 50° C. being from 1:0.8 to 1:1.2; and
2) a ratio of:
a viscosity of a neutral viscous aqueous solution containing 1% by mass of the (meth)acrylic acid/alkyl (meth)acrylate ester copolymer and 1% by mass of sodium chloride at 25° C. to:
a viscosity of a neutral viscous aqueous solution containing 1% by mass of the (meth)acrylic acid/alkyl (meth)acrylate ester copolymer and 0.5% by mass of sodium chloride at 25° C.
being from 1:0.75 to 1:1.25.

Item 2. The (meth)acrylic acid/alkyl (meth)acrylate ester copolymer according to Item 1, wherein the alkyl (meth)acrylate ester of which alkyl group has 18 to 24 carbon atoms is at least one member selected from the group consisting of stearyl methacrylate, eicosanyl methacrylate, behenyl methacrylate, and tetracosanyl methacrylate.

Item 3. The (meth)acrylic acid/alkyl (meth)acrylate ester copolymer according to Item 1 or 2, wherein the compound having two or more ethylenically unsaturated groups is at least one member selected from the group consisting of pentaerythritol allyl ether, diethylene glycol diallyl ether, polyethylene glycol diallyl ether, and polyallyl saccharose.

Item 4. Cosmetics blended with the (meth)acrylic acid/alkyl (meth)acrylate ester copolymer as defined in any one of Items 1 to 3.

Item 5. The cosmetics according to Item 4, characterized in that the cosmetics are further blended with an electrolyte.

Effects of the Invention

According to the present invention, a (meth)acrylic acid/alkyl (meth)acrylate ester copolymer capable of forming a neutral viscous aqueous solution having a high viscosity without being affected by temperature and electrolyte concentration, even in the presence of an electrolyte having a relatively high concentration, and cosmetics blended with the copolymer are provided.

BEST MODE FOR CARRYING OUT THE INVENTION

The present invention will be explained more specifically hereinbelow.

In the present invention, acrylic acid and methacrylic acid are collectively referred to as (meth)acrylic acid. Also, the term "(meth)acrylic acid/alkyl (meth)acrylate ester copolymer" means a copolymer of (meth)acrylic acid and an alkyl (meth)acrylate ester.

In addition, in the present invention, the word "neutral" in the neutral viscous aqueous solution means that a pH of the solution is from 6.5 to 7.5.

The (meth)acrylic acid/alkyl (meth)acrylate ester copolymer of the present invention contains as constituents:

95.42 to 97.48% by mass of (meth)acrylic acid, 2.43 to 4.30% by mass of an alkyl (meth)acrylate ester of which alkyl group has 18 to 24 carbon atoms, and 0.08 to 0.30% by mass of a compound having two or more ethylenically unsaturated groups.

The alkyl (meth)acrylate ester of which alkyl group has 18 to 24 carbon atoms, usable in the present invention refers to an ester formed between (meth)acrylic acid and a higher alcohol of which alkyl group has 18 to 24 carbon atoms, and includes, for example, an ester formed between (meth)acrylic acid and stearyl alcohol, an ester formed between (meth)acrylic acid and eicosanol, an ester formed between (meth)acrylic acid and behenyl alcohol, an ester formed between (meth)acrylic acid and tetracosanol, and the like. These alkyl (meth)acrylate esters may be used alone or in a mixture of two or more kinds. Specific examples include at least one member, i.e. alone or a mixture of these components, selected from the group consisting of eicosanyl (meth)acrylate, behenyl (meth)acrylate, and tetracosanyl (meth)acrylate; or a mixture of two to four members selected from the group consisting of stearyl (meth) acrylate, eicosanyl (meth)acrylate, behenyl (meth)acrylate, and tetracosanyl (meth)acrylate, and a preferred example includes a mixture of four members of stearyl (meth)acrylate, eicosanyl (meth)acrylate, behenyl (meth)acrylate, and tetracosanyl (meth)acrylate. Among them, stearyl methacrylate, eicosanyl methacrylate, behenyl methacrylate, and tetracosanyl methacrylate are suitably used, because of excellent viscosity properties and feel of the neutral viscous aqueous solution of the (meth)acrylic acid/alkyl (meth)acrylate ester copolymer obtained and the above solution in the presence of an electrolyte. More preferably, an alkyl (meth)acrylate ester containing at least behenyl methacrylate in an amount of 50% by mass or more is used. Here, as the alkyl (meth)acrylate ester of which alkyl group has 18 to 24 carbon atoms, for example, a commercially available product under the trade name of BLEMMER VMA70, manufactured by NOF or the like may be used.

As the combination of (meth)acrylic acid and the alkyl (meth)acrylate ester of which alkyl group has 18 to 24 carbon atoms usable in the present invention, each of them alone may be combined, or one of them or both that may be used together in a combination of two or more kinds.

The compound having two or more ethylenically unsaturated groups usable in the present invention is not particularly limited, and, for example, a compound of which ethylenically unsaturated groups are an allyl group is preferably used. Among them, pentaerythritol allyl ethers, such as pentaerythritol diallyl ether, pentaerythritol triallyl ether, and pentaerythritol tetraallyl ether, diethylene glycol diallyl ether, polyethylene glycol diallyl ether and polyallyl saccharose are even more preferably used. These compounds having two or more ethylenically unsaturated groups may be used alone or in a combination of two or more kinds.

The (meth)acrylic acid/alkyl (meth)acrylate ester copolymer of the present invention has a feature in a proportion of the amounts of the (meth)acrylic acid, the alkyl (meth)acrylate ester of which alkyl group has 18 to 24 carbon atoms, and the compound having two or more ethylenically unsaturated groups used during the polymerization. The proportion of each of the amount used will be explained hereinbelow. Here, the proportion of the amounts used is a value, supposing that a total amount of the (meth)acrylic acid, the alkyl (meth) acrylate ester of which alkyl group has 18 to 24 carbon atoms, and the compound having two or more ethylenically unsaturated groups used is 100% by mass.

The proportion of the amount of the (meth)acrylic acid used is from 95.42 to 97.48% by mass, preferably from 95.47 to 97.46% by mass, and more preferably from 95.97 to 96.94% by mass. When the proportion of the amount of the (meth)acrylic acid used is less than 95.42% by mass, upon the preparation of the neutral viscous aqueous solution, the viscosity of the solution in the presence of an electrolyte in a low concentration becomes markedly high, so that a rate of change in viscosity at a given electrolyte concentration becomes large, thereby making it difficult to use the solution. On the other hand, when the proportion of the amount of the (meth)acrylic acid used exceeds 97.48% by mass, upon the preparation of the neutral viscous aqueous solution, a sufficient viscosity cannot be obtained in the presence of an electrolyte, so that a rate of change in viscosity due to temperature and electrolyte concentration becomes large, thereby making it difficult to use the solution.

The proportion of the amount of the alkyl (meth)acrylate ester of which alkyl group has 18 to 24 carbon atoms used is from 2.43 to 4.30% by mass, and preferably from 2.91 to 3.84% by mass. When the proportion of the amount of the alkyl (meth)acrylate ester of which alkyl group has 18 to 24 carbon atoms used is less than 2.43% by mass, upon the preparation of the neutral viscous aqueous solution, a sufficient viscosity cannot be obtained in the presence of an electrolyte, so that a rate of change in viscosity due to temperature and electrolyte concentration becomes large, thereby making it difficult to use the solution. On the other hand, when the proportion of the amount of the alkyl (meth)acrylate ester of which alkyl group has 18 to 24 carbon atoms used exceeds 4.30% by mass, upon the preparation of the neutral viscous aqueous solution, the viscosity of the solution in the presence of an electrolyte in a low concentration becomes markedly high, so that a rate of change in viscosity at a given electrolyte concentration becomes large, thereby making it difficult to use the solution.

The proportion of the amount of the compound having two or more ethylenically unsaturated groups used is from 0.08 to 0.30% by mass, preferably from 0.11 to 0.24% by mass, and more preferably from 0.15 to 0.19% by mass. When the proportion of the amount of the compound having two or more ethylenically unsaturated groups used is less than 0.08% by mass, upon the preparation of the neutral viscous aqueous solution, a sufficient viscosity cannot be obtained in the presence of an electrolyte, so that a rate of change in viscosity due to temperature and electrolyte concentration becomes large, thereby making it difficult to use the solution. On the other hand, when the proportion of the amount of the compound having two or more ethylenically unsaturated groups used exceeds 0.30% by mass, upon the preparation of the neutral viscous aqueous solution, the viscosity of the solution in the presence of an electrolyte in a low concentration becomes high, so that a rate of change in viscosity at a given electrolyte concentration becomes large, thereby making it difficult to use the solution.

In the present invention, a method of obtaining a (meth) acrylic acid/alkyl (meth)acrylate ester copolymer including the step of polymerizing the (meth)acrylic acid, the alkyl (meth)acrylate ester of which alkyl group has 18 to 24 carbon atoms, and the compound having two or more ethylenically unsaturated groups is not particularly limited, and an ordinary method, such as a method including step of polymerizing these raw materials in an inert gas atmosphere using a polymerization initiator while stirring in a solvent, can be employed.

The inert gas for obtaining an inert gas atmosphere includes, for example, a nitrogen gas, an argon gas, and the like.

The above-mentioned solvent is not particularly limited, so long as the solvent is a substance that dissolves the (meth) acrylic acid, the alkyl (meth)acrylate ester of which alkyl group has 18 to 24 carbon atoms, and the compound having two or more ethylenically unsaturated groups, but the solvent does not dissolve the resulting (meth)acrylic acid/alkyl (meth)acrylate ester copolymer and does not inhibit the reaction. Specific examples of the solvent include hydrocarbon solvents, such as normal-pentane, normal-hexane, normal-heptane, cyclopentane and cyclohexane. These solvents can be used alone or in a mixture of two or more kinds. Among them, normal-hexane and normal-heptane are suitably used. In addition, these hydrocarbon solvents can be used in a combination with an organic solvent such as a ketone, an ester, an ether, and a saturated alcohol. Preferred specific examples of the organic solvent include methyl acetate, ethyl acetate, isopropyl acetate, propyl acetate, butyl acetate, methyl ethyl ketone, butyl propionate, cyclohexanone, and the like.

The amount of the solvent used is preferably from 300 to 5000 parts by mass, based on 100 parts by mass of the (meth) acrylic acid, from the viewpoint of improving stirring operability and from the viewpoint of economic advantages.

The above-mentioned polymerization initiator is, for example, preferably a radical polymerization initiator. Specific examples thereof include $\alpha,\alpha'$-azoisobutyronitrile, 2,2'-azobis-2,4-dimethylvaleronitrile, 2,2'-azobismethylisobutyrate, and the like. Among them, 2,2'-azobismethylisobutyrate is suitably used, from the viewpoint of obtaining a (meth)acrylic acid/alkyl (meth)acrylate ester copolymer having a large molecular weight.

It is desired that the amount of the polymerization initiator used is from 0.00003 to 0.002 mol, per 1 mol of the (meth) acrylic acid. When the amount of the polymerization initiator used is less than 0.00003 mol, the reaction rate is delayed, so that there is a risk of not being economic advantageous. On the other hand, when the amount of the polymerization initiator used exceeds 0.002 mol, the polymerization vigorously progresses, so that there is a risk that the reaction control would be made difficult.

The reaction temperature is preferably from 50° to 90° C., and more preferably from 55° to 75° C. When the reaction temperature is less than 50° C., the viscosity of the reaction solution increases, so that there is a risk that homogeneous stirring of the reaction solution would be made difficult. On the other hand, when the reaction temperature exceeds 90° C., the reaction vigorously progresses, so that there is a risk that the reaction control would be made difficult. The reaction time cannot be unconditionally said because the reaction time depends upon the reaction temperature, and the reaction time is usually from 0.5 to 5 hours.

After the termination of the reaction, the reaction solution is heated to, for example, 80° to 130° C. to dissipate and remove the above-mentioned solvent, whereby a (meth) acrylic acid/alkyl (meth)acrylate ester copolymer of the present invention can be obtained. When the heating temperature is less than 80° C., there is a risk that a long period of time would be required in drying, and when the heating temperature exceeds 130° C., there is a risk that the solubility of the resulting (meth)acrylic acid/alkyl (meth)acrylate ester copolymer in water would be impaired.

The (meth)acrylic acid/alkyl (meth)acrylate ester copolymer thus obtained has the features that:

1) a viscosity of a neutral viscous aqueous solution containing 1% by mass of the (meth)acrylic acid/alkyl (meth)acrylate ester copolymer and 1% by mass of sodium chloride being 40000 mPa·s or more at 25° C., and a ratio of a viscosity of the neutral viscous aqueous solution at 25° C. to a viscosity of the neutral viscous aqueous solution at 50° C. (rate of change in viscosity) being from 1:0.8 to 1:1.2; and 2) a ratio of:
a viscosity of a neutral viscous aqueous solution containing 1% by mass of the (meth)acrylic acid/alkyl (meth)acrylate ester copolymer and 1% by mass of sodium chloride at 25° C. to:
a viscosity of a neutral viscous aqueous solution containing 1% by mass of the (meth)acrylic acid/alkyl (meth)acrylate ester copolymer and 0.5% by mass of sodium chloride at 25° C. (rate of change in viscosity) being from 1:0.75 to 1:1.25.

In other words, the (meth)acrylic acid/alkyl (meth)acrylate ester copolymer having the above-mentioned properties, obtainable by polymerizing each of monomers of 95.42 to 97.48% by mass of (meth)acrylic acid, 2.43 to 4.30% by mass of an alkyl (meth)acrylate ester of which alkyl group has 18 to 24 carbon atoms, and 0.08 to 0.30% by mass of a compound having two or more ethylenically unsaturated groups is also embraced in the present invention.

Here, the above-mentioned viscosity is a value as measured by the measurement method described later.

The viscosity of a neutral viscous aqueous solution containing 1% by mass of the (meth)acrylic acid/alkyl (meth) acrylate ester copolymer of the present invention and 1% by mass of sodium chloride is preferably 40000 mPa·s or more, and more preferably 42000 mPa·s or more at 25° C., from viewpoint of being capable of thickening in a smaller amount in order to obtain a moist and vitalizing feel without stickiness upon its use in cosmetics.

The ratio of a viscosity of a neutral viscous aqueous solution containing 1% by mass of the (meth)acrylic acid/alkyl (meth)acrylate ester copolymer of the present invention and 1% by mass of sodium chloride at 25° C. to a viscosity of the neutral viscous aqueous solution at 50° C. is preferably from 1:0.8 to 1:1.2, and more preferably from 1:0.9 to 1:1.1, from the viewpoint being less likely to be affected by air temperature fluctuations upon its use in cosmetics.

The ratio of a viscosity of a neutral viscous aqueous solution containing 1% by mass of the (meth)acrylic acid/alkyl (meth)acrylate ester copolymer of the present invention and 1% by mass of sodium chloride at 25° C. to a viscosity of the neutral viscous aqueous solution containing 0.5% by mass of sodium chloride at 25° C. is preferably from 1:0.75 to 1:1.25, and more preferably from 1:0.90 to 1:20, from the viewpoint of being able to apply in various blending compositions of different electrolyte concentrations upon its use in cosmetics.

The (meth)acrylic acid/alkyl (meth)acrylate ester copolymer of the present invention can be used as a thickener for cosmetics, or the like by, for example, dissolving the copolymer in pure water such as deionized water, neutralizing the solution with an alkali, to prepare a neutral viscous aqueous solution having a copolymer concentration of 1% by mass or so and a pH of from 6.5 to 7.5. In other words, a thickener containing the (meth)acrylic acid/alkyl (meth)acrylate ester copolymer of the present invention is also embraced by the present invention. The alkali used for neutralization is not particularly limited, and includes an alkali metal hydroxide such as sodium hydroxide, an amine such as triethanolamine or diisopropanolamine, and the like. Among them, sodium hydroxide is suitably used. The amount of (meth)acrylic acid/alkyl (meth)acrylate ester copolymer of the present invention blended to the cosmetics is not particularly limited so long as the desired effects are exhibited. For example, the copolymer is blended in an amount of preferably from 0.01 to 5.0% by mass, more preferably from 0.05 to 3.0% by mass, and even more preferably from 0.1 to 1.5% by mass, of the cosmetics. The amount of the copolymer blended is preferably 0.01% by mass or more, from the viewpoint of a thickening effect, and the amount of the copolymer blended is preferably 5% by mass or less, from the viewpoint of a smooth feel upon use without stickiness.

The neutral viscous aqueous solution obtained from the (meth)acrylic acid/alkyl (meth)acrylate ester copolymer of the present invention has a stable viscosity that does not depend on its concentration or temperature, even in the presence of an electrolyte in a relatively high concentration, and further has a moist and vitalizing feel without stickiness.

Although the reason why the (meth)acrylic acid/alkyl (meth)acrylate ester copolymer of the present invention has the properties as described above is not elucidated, it is deduced to be caused by the fact that each of the (meth)acrylic acid, the alkyl (meth)acrylate ester of which alkyl group has 18 to 24 carbon atoms, and the compound having two or more ethylenically unsaturated groups is used in a specified amount. For example, it is deduced that since each of the alkyl groups having 18 to 24 carbon atoms introduced into the (meth)acrylic acid/alkyl (meth)acrylate ester copolymer forms an association entity by hydrophobic interactions in the aqueous solution, the thickening increases, so that the influence by the electrolyte is reduced. In addition, it is deduced that since the compound having two or more ethylenically unsaturated groups introduced into the (meth)acrylic acid/alkyl (meth)acrylate ester copolymer functions as a crosslinking agent, the viscosity increases and at the same time a degree of freedom in hydrophobic interactions is lowered, thereby reducing the influence by temperature.

Therefore, by using the (meth)acrylic acid/alkyl (meth) acrylate ester copolymer of the present invention, cosmetics or the like having a stable viscosity that does not depend upon its concentration or temperature, even in the presence of an electrolyte in a relatively high concentration, and having a moist and vitalizing feel without stickiness can be produced.

The electrolyte usable in the present invention refers to a compound that ionically dissociates in water. The kinds of the electrolyte are not particularly limited, and include acid agents, such as carboxylic acids, such as lactic acid, gluconic acid, succinic acid, glutaric acid, adipic acid, malic acid, tartaric acid, maleic acid, fumaric acid, itaconic acid, citric acid, phthalic acid, acetic acid, benzoic acid, salicylic acid, gallic acid, and diethylbarbituric acid, amino acids, such as glycine, alanine, valine, leucine, serine, glutamic acid, and aspartic acid, organosulfonic acids, such as ethanesulfonic acid, phenolsulfonic acid, p-toluenesulfonic acid, and m-xylenesulfonic acid, aminosulfonic acids, such as taurine, and inorganic acids, such as hydrochloric acid; alkalizing agents, such as alkanolamines, such as monoethanolamine, diethanolamine, and triethanolamine, and inorganic bases, such as ammonia, sodium hydroxide, and potassium hydroxide; neutralized salts formed between the acid agents and the alkalizing agents mentioned above, for example, sodium chloride, potassium chloride, sodium citrate, potassium citrate, sodium benzoate, potassium benzoate, ammonium chloride, sodium carbonate, potassium carbonate, sodium hydrogenphosphate, potassium hydrogenphosphate, monoethanolamine sulfate, No. 1 sodium silicate, No. 2 sodium silicate, No. 3 sodium silicate, and other active ingredients such as ascorbic acid and a derivative thereof, dipotassium glycyrrhizate. Among them, lactic acid, malic acid, maleic acid, citric acid, benzoic acid, salicylic acid, an amino acid such as glycine, alanine, valine, leucine, serine, glutamic acid, or aspartic acid, monoethanolamine, diethanolamine, triethanolamine, sodium hydroxide, potassium hydroxide, sodium chloride, potassium chloride, sodium citrate, potassium citrate, ascorbic acid and a derivative thereof, and dipotassium glycyrrhizate are preferably used, and lactic acid, citric acid, sodium citrate, sodium hydroxide, sodium chloride, potassium chloride, ascorbic acid and a derivative thereof, and dipotassium glycyrrhizate are especially preferably used, from the viewpoint of stable blending to cosmetics, water-retaining property upon application to skin, moisture-retaining property and the like. The amount to be blended is preferably from 1000 to 1 part by mass, and especially preferably from 500 to 5 parts by mass, based on 100 parts by mass of the (meth)acrylic acid/alkyl (meth)acrylate ester copolymer.

The cosmetics of the present invention include, for example, lotion, emulsion, essence, cream, cream pack, massage cream, cleansing cream, cleansing gel, facial wash foam, clear shampoo, pearly shampoo, body shampoo, hair-setting gel, sunscreen, styling gel, eyeliner, mascara, lipstick, foundation, and the like.

In addition, since the neutral viscous aqueous solution has a relatively low viscosity in a state that an electrolyte is not present, the neutral viscous aqueous solution can be said to be a very useful thickener, from the viewpoint of production efficiency of cosmetics and the like. In other words, in various production steps of manufactured articles, by providing a solution having a low viscosity prior to adding an electrolyte and providing a step of adding an electrolyte as a later-staged step, the operating efficiencies in the reaction step, the transporting step, the heating step, the blending step, and the like, prior to adding an electrolyte can be remarkably improved.

The present invention will be specifically described hereinbelow by giving Examples and Comparative Examples, without intending to limit the scope of the present invention thereto.

[Measurement Methods]

In order to evaluate the properties of the (meth)acrylic acid/alkyl (meth)acrylate ester copolymer obtained in each of Examples and Comparative Examples as a thickener, the viscosity was measured by the following method by preparing a neutral viscous aqueous solution having a given sodium chloride concentration (evaluation sample).

(1) Preparation of Evaluation Sample

A 2-L beaker made of SUS was charged with 1960 g of purified water, and 40 g of a (meth)acrylic acid/alkyl (meth) acrylate ester copolymer obtained in each of Examples 1 to 8 and Comparative Examples 1 to 6 was gently supplied into a bench-type DISPER (manufactured by TOKUSHU KIKA KOGYO Co., Ltd., T.K. ROBOMICS) under the conditions of 2000 rotations per minute, to immerse the (meth)acrylic acid/alkyl (meth)acrylate ester copolymer in water. Next, the contents were transferred to a Mizuho vacuum emulsification apparatus (manufactured by MIZUHO INDUSTRIAL CO., LTD., model: PVQ-5), and stirred for 90 minutes under the conditions of a paddle blade part at 60 rotations per minute, a blade part of DISPER at 3000 rotations per minute, an internal temperature of 80° C., and a tightly sealed, reduced pressure. After stirring, the contents were transferred to a 2-L beaker made of SUS, and tightly sealed, and allowed to stand for a whole day to return to an ambient temperature.

The resulting solution was divided in smaller portions of 100 g each into 300 mL beakers, and 15 g of a 6% by mass aqueous sodium hydroxide solution was added thereto, and the mixture was stirred with the above-mentioned bench-type DISPER for 1 minute under conditions of 3,000 rotations per minute, to give a neutral viscous aqueous solution of which pH (25° C.) was from 6.5 to 7.5.

Five samples each prepared by adding a 10% by mass aqueous sodium chloride solution and purified water to the resulting neutral viscous aqueous solution so that the mass of the sample was 200 g and the concentration of the sodium chloride in the sample was 1% by mass, and one sample each prepared by adding a 10% by mass aqueous sodium chloride solution and purified water to the resulting neutral viscous aqueous solution so that the concentrations of the sodium chloride were 0.25% by mass, 0.5% by mass, and 0.75% by mass were furnished.

The samples prepared were each stirred for 5 minutes with the bench-type DISPER mentioned above under conditions of 3000 rotations per minute, and the dispersion was then defoamed with DALTON Universal Mixer-Agitator (model: 5DMV-01-r, manufactured by DALTON CORPORATION) under a reduced pressure. Five samples of which sodium chloride concentration after defoaming was 1% by mass were allowed to stand over one day in a water bath set at 5° C., 15° C., 25° C., 40° C., and 50° C., respectively, to provide samples to be evaluated. In addition, the samples of which sodium chloride concentrations were 0.25% by mass, 0.5% by mass, and 0.75% by mass were allowed to stand over one day in a water bath set at 25° C., to provide samples to be evaluated.

(2) Viscosity Measurement

The viscosity after 1 minute for each of the samples to be evaluated was measured at each temperature using a BL-type rotary viscometer (DEGITAL VISMETRON, manufactured by SHIBAURA SYSTEMS CO., LTD.) with a rotational speed of a spindle rotor No. 4 of 6 rotations per minute. The measurement results are shown in Tables 2 and 3.

Example 1

A 500-mL four-necked flask equipped with a stirrer, a thermometer, a nitrogen inlet tube, and a condenser was charged with 45 g of acrylic acid (0.625 mol), 1.35 g of BLEMMER VMA70 (manufactured by NOF Corporation: a mixture containing 10 to 20 parts by mass of stearyl methacrylate, 10 to 20 parts by mass of eicosanyl methacrylate, 59 to 80 parts by mass of behenyl methacrylate, and 1 part by mass or less of tetracosanyl methacrylate) as an alkyl acrylate ester, of which alkyl group has 18 to 24 carbon atoms, 0.05 g of pentaerythritol allyl ether, 150 g of normal-hexane, and 0.081 g of 2,2'-azobismethylisobutyrate (0.00035 mol). Subsequently, the mixture was homogeneously mixed while stirring, and a nitrogen gas was then blown into the solution in order to remove oxygen existing in the upper spatial region of the reaction vessel, raw materials and the solvents. Next, the mixture was reacted for 4 hours in a nitrogen atmosphere while keeping the temperature at 60° to 65° C. After the termination of the reaction, the formed slurry was heated to 90° C. to distill off normal-hexane, and further dried under a reduced pressure at 110° C. and 10 mmHg for 8 hours, to thereby give 43 g of a (meth)acrylic acid/alkyl (meth)acrylate ester copolymer in the form of a white fine powder.

Example 2

The same procedures as in Example 1 were carried out, except for changing the amount of BLEMMER VMA70 (manufactured by NOF Corporation) used to 1.58 g, to give 44 g of a (meth)acrylic acid/alkyl (meth)acrylate ester copolymer in the form of a white fine powder.

Example 3

The same procedures as in Example 1 were carried out, except for changing the amount of BLEMMER VMA70 (manufactured by NOF Corporation) used to 1.80 g, to give 45 g of a (meth)acrylic acid/alkyl (meth)acrylate ester copolymer in the form of a white fine powder.

Example 4

The same procedures as in Example 1 were carried out, except for changing the amount of pentaerythritol allyl ether used to 0.07 g, to give 43 g of a (meth)acrylic acid/alkyl (meth)acrylate ester copolymer in the form of a white fine powder.

Example 5

The same procedures as in Example 1 were carried out, except for changing the amount of BLEMMER VMA70 (manufactured by NOF Corporation) used to 1.58 g and the amount of pentaerythritol allyl ether used to 0.07 g, to give 44 g of a (meth)acrylic acid/alkyl (meth)acrylate ester copolymer in the form of a white fine powder.

Example 6

The same procedures as in Example 1 were carried out, except for changing the amount of pentaerythritol allyl ether used to 0.09 g, to give 42 g of a (meth)acrylic acid/alkyl (meth)acrylate ester copolymer in the form of a white fine powder.

Example 7

The same procedures as in Example 1 were carried out, except for changing the amount of BLEMMER VMA70 (manufactured by NOF Corporation) used to 1.80 g and the amount of pentaerythritol allyl ether used to 0.09 g, to give 44 g of a (meth)acrylic acid/alkyl (meth)acrylate ester copolymer in the form of a white fine powder.

Example 8

The same procedures as in Example 1 were carried out, except for changing the amount of pentaerythritol allyl ether used to 0.14 g, to give 43 g of a (meth)acrylic acid/alkyl (meth)acrylate ester copolymer in the form of a white fine powder.

Comparative Example 1

The same procedures as in Example 1 were carried out, except for changing the amount of pentaerythritol allyl ether used to 0.02 g, to give 43 g of a (meth)acrylic acid/alkyl (meth)acrylate ester copolymer in the form of a white fine powder.

Comparative Example 2

The same procedures as in Example 1 were carried out, except for changing the amount of BLEMMER VMA70 (manufactured by NOF Corporation) used to 0.99 g and the amount of pentaerythritol allyl ether used to 0.09 g, to give 42 g of a (meth)acrylic acid/alkyl (meth)acrylate ester copolymer in the form of a white fine powder.

Comparative Example 3

The same procedures as in Example 1 were carried out, except for changing the amount of BLEMMER VMA70 (manufactured by NOF Corporation) used to 2.25 g and the amount of pentaerythritol allyl ether used to 0.09 g, to give 45 g of a (meth)acrylic acid/alkyl (meth)acrylate ester copolymer in the form of a white fine powder.

Comparative Example 4

The same procedures as in Example 1 were carried out, except for changing the amount of pentaerythritol allyl ether used to 0.18 g, to give 43 g of a (meth)acrylic acid/alkyl (meth)acrylate ester copolymer in the form of a white fine powder.

Comparative Example 5

The same procedures as in Example 1 were carried out, except for changing 1.35 g of BLEMMER VMA70 (manufactured by NOF Corporation) to 1.35 g of stearyl methacrylate, and changing the amount of pentaerythritol allyl ether used to 0.09 g, to give 42 g of a (meth)acrylic acid/alkyl (meth)acrylate ester copolymer in the form of a white fine powder.

Comparative Example 6

The same procedures as in Example 1 were carried out, except for changing 1.35 g of BLEMMER VMA70 (manufactured by NOF Corporation) to 1.35 g of stearyl methacrylate, and changing the amount of pentaerythritol allyl ether used to 0.14 g, to give 43 g of a (meth)acrylic acid/alkyl (meth)acrylate ester copolymer in the form of a white fine powder.

The major raw materials used in Examples 1 to 8 and Comparative Examples 1 to 6 and the proportions of the amounts used are shown in Table 1.

TABLE 1

| | (Meth)acrylic Acid | | Alkyl (Meth)acrylate Ester | | Compounds Having Two or More Ethylenically Unsaturated Groups | |
|---|---|---|---|---|---|---|
| | Kinds | Proportion of Amount Used [% by mass] | Kinds | Proportion of Amount Used [% by mass] | Kinds | Proportion of Amount Used [% by mass] |
| Ex. 1 | Acrylic acid | 96.98 | BLEMMER VMA70 | 2.91 | Pentaerythritol allyl ether | 0.11 |
| Ex. 2 | Acrylic acid | 96.50 | BLEMMER VMA70 | 3.39 | Pentaerythritol allyl ether | 0.11 |
| Ex. 3 | Acrylic acid | 96.05 | BLEMMER VMA70 | 3.84 | Pentaerythritol allyl ether | 0.11 |
| Ex. 4 | Acrylic acid | 96.94 | BLEMMER VMA70 | 2.91 | Pentaerythritol allyl ether | 0.15 |
| Ex. 5 | Acrylic acid | 96.46 | BLEMMER VMA70 | 3.39 | Pentaerythritol allyl ether | 0.15 |
| Ex. 6 | Acrylic acid | 96.90 | BLEMMER VMA70 | 2.91 | Pentaerythritol allyl ether | 0.19 |
| Ex. 7 | Acrylic acid | 95.97 | BLEMMER VMA70 | 3.84 | Pentaerythritol allyl ether | 0.19 |
| Ex. 8 | Acrylic acid | 96.80 | BLEMMER VMA70 | 2.90 | Pentaerythritol allyl ether | 0.30 |
| Comp. Ex. 1 | Acrylic acid | 97.05 | BLEMMER VMA70 | 2.91 | Pentaerythritol allyl ether | 0.04 |
| Comp. Ex. 2 | Acrylic acid | 97.66 | BLEMMER VMA70 | 2.15 | Pentaerythritol allyl ether | 0.19 |
| Comp. Ex. 3 | Acrylic acid | 95.06 | BLEMMER VMA70 | 4.75 | Pentaerythritol allyl ether | 0.19 |
| Comp. Ex. 4 | Acrylic acid | 96.71 | BLEMMER VMA70 | 2.90 | Pentaerythritol allyl ether | 0.39 |
| Comp. Ex. 5 | Acrylic acid | 96.90 | Stearyl methacrylate | 2.91 | Pentaerythritol allyl ether | 0.19 |
| Comp. Ex. 6 | Acrylic acid | 96.80 | Stearyl methacrylate | 2.90 | Pentaerythritol allyl ether | 0.30 |

TABLE 2

| | Viscosity [mPa · s] (NaCl: 1% by Mass being added, Temperature Variations: ° C.) | | | | | Ratio of Viscosities (at 25° C.: at 50° C.) |
|---|---|---|---|---|---|---|
| | 5 | 15 | 25 | 40 | 50 | |
| Ex. 1 | 53800 | 52900 | 43100 | 42400 | 35500 | 1:0.82 |
| Ex. 2 | 79700 | 74300 | 58100 | 76800 | 68200 | 1:1.17 |
| Ex. 3 | 78000 | 77300 | 62100 | 72700 | 72800 | 1:1.17 |
| Ex. 4 | 63900 | 61200 | 61100 | 63800 | 58100 | 1:0.95 |
| Ex. 5 | 68200 | 64900 | 58100 | 62400 | 58500 | 1:1.01 |
| Ex. 6 | 51300 | 48100 | 43800 | 47100 | 45500 | 1:1.04 |
| Ex. 7 | 70600 | 66400 | 55100 | 63800 | 61000 | 1:1.07 |

TABLE 2-continued

| | Viscosity [mPa·s] (NaCl: 1% by Mass being added, Temperature Variations: °C.) | | | | | Ratio of Viscosities (at 25° C.: at 50° C.) |
|---|---|---|---|---|---|---|
| | 5 | 15 | 25 | 40 | 50 | |
| Ex. 8 | 48100 | 48000 | 41800 | 44200 | 43000 | 1:1.03 |
| Comp. Ex. 1 | 40400 | 29400 | 26900 | 8300 | 100 | 1:0.004 |
| Comp. Ex. 2 | 30500 | 20000 | 18000 | 1000 | 100 | 1:0.006 |
| Comp. Ex. 3 | 74700 | 74300 | 48500 | 72600 | 64900 | 1:1.34 |
| Comp. Ex. 4 | 46600 | 46100 | 42000 | 46300 | 44000 | 1:1.05 |
| Comp. Ex. 5 | 34200 | 31500 | 30500 | 29600 | 26500 | 1:0.87 |
| Comp. Ex. 6 | 38500 | 38600 | 39900 | 47800 | 48600 | 1:1.22 |

TABLE 3

| | Viscosity [mPa·s] (Temp.: 25° C., Change in Amount of NaCl: % by mass) | | | | Ratio of Viscosities (1:0.5 parts by mass) |
|---|---|---|---|---|---|
| | 0.25 | 0.5 | 0.75 | 1 | |
| Ex. 1 | 23800 | 42100 | 45100 | 43100 | 1:0.98 |
| Ex. 2 | 62000 | 68000 | 62100 | 58100 | 1:1.17 |
| Ex. 3 | 78400 | 70100 | 62900 | 62100 | 1:1.13 |
| Ex. 4 | 44000 | 57400 | 57000 | 61100 | 1:0.94 |
| Ex. 5 | 53000 | 62600 | 58700 | 58100 | 1:1.08 |
| Ex. 6 | 34600 | 44900 | 43300 | 43800 | 1:1.03 |
| Ex. 7 | 61800 | 63000 | 64000 | 55100 | 1:1.14 |
| Ex. 8 | 49400 | 52000 | 49200 | 41800 | 1:1.24 |
| Comp. Ex. 1 | 1300 | 9500 | 17600 | 26900 | 1:0.35 |
| Comp. Ex. 2 | 50 | 100 | 7000 | 18000 | 1:0.006 |
| Comp. Ex. 3 | 100000 | 100000 | 78600 | 48500 | 1:2.06 |
| Comp. Ex. 4 | 64300 | 64500 | 53300 | 42000 | 1:1.54 |
| Comp. Ex. 5 | 12500 | 19100 | 36400 | 30500 | 1:0.63 |
| Comp. Ex. 6 | 28100 | 31400 | 53600 | 39900 | 1:0.79 |

It can be seen from Tables 2 and 3 that the (meth)acrylic acid/alkyl (meth)acrylate ester copolymers obtained in Examples 1 to 8 form a neutral viscous aqueous solution having a high viscosity without being affected by temperature or electrolytic concentrations, even in the presence of the electrolyte.

As described above, it was shown that the (meth)acrylic acid/alkyl (meth)acrylate ester copolymers obtained in Examples 1 to 8 mentioned above can be utilized as thickeners having excellent properties as mentioned above.

Preparation Examples of Cosmetics, Such as Lotion, Emulsion, essence, cream, cream pack, massage cream, cleansing cream, cleansing gel, facial wash foam, sunscreen, styling gel, eyeliner, mascara, lipstick, foundation, clear shampoo, pearly shampoo, body shampoo, and hair-setting gel, in which the (meth)acrylic acid/alkyl (meth)acrylate ester copolymer of the present invention was used, will be illustrated hereinafter.

The above-mentioned cosmetics can appropriately contain components usable in ordinary cosmetics listed in Iyakubugaihin Genryo Kikaku (Quasi-Drug Raw Material Standards) 2006 (published by YAKUJI NIPPO), such as an oil agent, a surfactant, a polyhydric alcohol, a water-soluble polymer, a moisture-retaining agent, an agent against whitening, inflammation, spots or hair damages, a blood circulation enhancer, a softening agent, a subcorneal protecting agent, an ultraviolet inhibitor, an antiseptic agent, a pH adjustment agent, a perfume, an antioxidant, a coloring agent, and an electrolytic component, within the range that would not impair the effects of the present technique.

Example 9

Each of Ingredients 1 to 6 listed below was homogeneously stirred and mixed in respective proportions, and each of Ingredients 7 to 10 was further added, and homogeneously stirred to allow solubilization of the mixture to prepare a lotion. The unit (%) of the amount blended is expressed as % by mass.
1. (Meth)acrylic acid/alkyl (meth)acrylate ester copolymer (Example 1): 0.1%
2. Sodium hydroxide: 0.28%
3. Ascorbic acid 2-glucoside: 2.0%
4. Citric acid: 0.01%
5. Sodium hydrogenphosphate: 0.1%
6. Purified water: proportion totaling to 100%
7. Ethanol: 8.0%
8. Polyoxyethylene polyoxypropylene decyl tetradecyl ether (30EO, 6PO): 0.3%
9. Antiseptic agent: 0.1%
10. Perfume: proper amount The lotion prepared according to the above composition had a moist and vitalizing feel without stickiness, and also excellent stability with time. On the other hand, the lotion blended with the copolymer of Comparative Example 1 in place of the copolymer of Example 1 had a worsened feel due to aggregation of the copolymer, and had insufficient stability with time.

Example 10

Ingredients 1 to 8 and Ingredients 9 to 17 listed below are mixed in respective proportions while stirring, and each mixture is heated to 80° C. The latter ingredient mixture is added dropwise to the former ingredient mixture while stirring to emulsify the mixture. Subsequently, the emulsion was cooled, to prepare an emulsion.
1. Polyoxyethylene sorbitan monostearate (20 EO): 1.0%
2. Polyoxypropylene sorbitol tetraoleate (40 PO): 1.5%
3. Lipophilic glycerol monostearate: 1.0%
4. Stearic acid: 0.5%
5. Behenyl alcohol: 1.5%
6. Squalane: 5.0%
7. Cetyl 2-ethylhexanoate: 5.0%
8. Dimethyl poly(siloxane): 0.5%
9. (Meth)acrylic acid/alkyl (meth)acrylate ester copolymer (Example 2): 0.1%
10. Xanthane gum: 0.1%
11. Sodium hydroxide: 0.05%
12. Sodium lactate: 1.0%
13. Citric acid: 0.01%
14. Sodium hydrogenphosphate: 0.1%
15. 1,3-Butylene glycol: 7.0%
16. Antiseptic agent: 0.15%
17. Purified water: proportion totaling to 100%

The emulsion prepared according to the above composition had a moist and vitalizing feel without stickiness, and also excellent stability with time. On the other hand, the emulsion blended with the copolymer of Comparative Example 2 in place of the copolymer of Example 2 had a worsened feel due to aggregation of the copolymer, and had insufficient stability with time.

Example 11

Ingredients 1 to 11 listed below were mixed in respective proportions at an ambient temperature to dissolve, while stirring, to give a viscous aqueous solution to prepare an essence.
1. (Meth)acrylic acid/alkyl (meth)acrylate ester copolymer (Example 3): 0.2%
2. Sodium hydroxide: 0.08%
3. Magnesium L-ascorbyl phosphate: 3.0%
4. Sodium citrate: 0.5%
5. EDTA (ethylenediaminetetraacetic acid) tetrasodium: 0.1%
6. 1,3-Butylene glycol: 7.0%
7. Glycerol: 8.0%
8. Purified water: proportion totaling to 100%
9. Sodium hyaluronate: 0.2%
10. Antiseptic agent: 0.15%
11. Ethanol: 5.0%

The essence prepared according to the above composition had a moist and vitalizing feel without stickiness, and also excellent stability with time. On the other hand, the essence blended with the copolymer of Comparative Example 3 in place of the copolymer of Example 3 had a worsened feel due to aggregation of the copolymer, and had insufficient stability with time.

Example 12

Ingredients 1 to 6 and Ingredients 7 to 14 listed below are mixed in respective proportions while stirring, and each mixture is heated to 80° C. The latter ingredient mixture is added dropwise to the former ingredient mixture while stirring to emulsify the mixture. Subsequently, the mixture was cooled, to give a cream.
1. Decaglycerol pentaoleate: 3.0%
2. Beeswax: 2.0%
3. Cetanol: 2.0%
4. Squalane: 5.0%
5. Glycerol tri-2-ethylhexanoate: 2.0%
6. Dimethyl poly(siloxane): 0.5%
7. Glycerol: 5.0%
8. Magnesium L-ascorbyl phosphate: 3.0%
9. Sodium citrate: 0.5%
10. EDTA (ethylenediaminetetraacetic acid) tetrasodium: 0.1%
11. (Meth)acrylic acid/alkyl (meth)acrylate ester copolymer (Example 4): 0.15%
12. Sodium hydroxide: 0.06%
13. Antiseptic agent: 0.1%
14. Purified water: proportion totaling to 100%

The cream prepared according to the above composition had a moist and vitalizing feel without stickiness, and also excellent stability with time. On the other hand, the cream blended with the copolymer of Comparative Example 4 in place of the copolymer of Example 4 had a worsened feel due to aggregation of the copolymer, and had insufficient stability with time.

Example 13

Ingredients 1 to 4 and Ingredients 5 to 12 listed below are mixed in respective proportions while stirring, and each mixture is heated to 80° C.

The latter ingredient mixture is added dropwise to the former ingredient mixture while stirring to emulsify the mixture. Subsequently, the mixture was cooled, to give a cream pack.
1. Polyoxyethylene polyoxypropylene cetyl ether (20EO, 4PO): 0.8%
2. Diglycerol monostearate: 0.2%
3. Glycerol tri-2-ethylhexanoate: 1.0%
4. Meadowfoam oil: 1.0%
5. Glycerol: 5.0%
6. 1,3-Butylene glycol: 3.0%
7. (Meth)acrylic acid/alkyl (meth)acrylate ester copolymer (Example 5): 0.1%
8. Sodium hydroxide: 0.28%
9. Hydroxyethyl cellulose: 0.3%
10. Ascorbic acid 2-glucoside: 2.0%
11. Antiseptic agent: 0.15%
12. Purified water: proportion totaling to 100%

The cream pack prepared according to the above composition had a moist and vitalizing feel without stickiness, and also excellent stability with time. On the other hand, the cream pack blended with the copolymer of Comparative Example 5 in place of the copolymer of Example 5 had a worsened feel due to aggregation of the copolymer, and had insufficient stability with time.

Example 14

Ingredients 1 to 7 and Ingredients 8 to 13 listed below are mixed in respective proportions while stirring, and each mixture is heated to 80° C.

The latter ingredient mixture is added dropwise to the former ingredient mixture while stirring to emulsify the mixture. Subsequently, the mixture was cooled, to give a massage cream.
1. Polyoxyethylene cetyl ether (20EO): 2.0%
2. Lipophilic glycerol monostearate: 4.0%
3. Cetanol: 2.0%
4. White Vaseline: 6.0%
5. Squalane: 30.0%
6. Glycerol tri-2-ethylhexanoate: 5.0%
7. Dimethyl poly(siloxane): 0.5%
8. (Meth)acrylic acid/alkyl (meth)acrylate ester copolymer (Example 6): 0.1%
9. Sodium hydroxide: 0.04%
10. Glycerol: 5.0%
11. Sodium pyrrolidonecarboxylate: 1.0%
12. Antiseptic agent: 0.15%
13. Purified water: proportion totaling to 100%

The massage cream prepared according to the above composition had a moist and vitalizing feel without stickiness, and also excellent massage smoothness and stability with time. On the other hand, the massage cream blended with the copolymer of Comparative Example 6 in place of the copolymer of Example 6 had a worsened feel due to aggregation of the copolymer, and had insufficient stability with time.

Example 15

Ingredients 1 to 7 and Ingredients 8 to 13 listed below are mixed in respective proportions while stirring, and each mixture is heated to 80° C. The latter ingredient mixture is added dropwise to the former ingredient mixture while stirring to emulsify the mixture. Subsequently, the mixture was cooled, to give a cleansing cream.
1. Polyoxyethylene sorbitan monostearate (20EO): 2.0%
2. Polyoxypropylene sorbitol tetraoleate (40PO): 1.0%

3. Self-emulsifiable glycerol monostearate: 2.0%
4. Stearic acid: 4.0%
5. Cetanol: 2.0%
6. Liquid paraffin: 30.0%
7. Glycerol tri-2-ethylhexanoate: 10.0%
8. 1,3-Butylene glycol: 5.0%
9. (Meth)acrylic acid/alkyl (meth)acrylate ester copolymer (Example 7): 0.1%
10. Sodium hydroxide: 0.04%
11. L-Serine: 1.0%
12. Antiseptic agent: 0.1%
13. Purified water: proportion totaling to 100%

The cleansing cream prepared according to the above composition had high cleansing function and a moist and vitalizing feel without stickiness, and also excellent stability with time. On the other hand, the cleansing cream blended with the copolymer of Comparative Example 1 in place of the copolymer of Example 7 had a worsened feel due to aggregation of the copolymer, and had insufficient cleansing function and stability with time.

Example 16

Ingredients 1 to 10 listed below were homogeneously mixed in respective proportions at an ambient temperature, to produce a gel-like state, to prepare a cleansing gel.
1. Carboxyvinyl polymer*1: 0.1%
   *1: AQUPEC HV-501E, manufactured by Sumitomo Seika Co., Ltd.
2. (Meth)acrylic acid/alkyl (meth)acrylate ester copolymer (Example 8): 0.1%
3. Sodium hydroxide: 0.08%
4. Sodium pyrrolidonecarboxylate: 1.0%
5. Hydroxypropyl cellulose: 0.5%
6. Polyoxyethylene cetyl ether (30EO): 16.0%
7. Polyoxyethylene lauryl ether (5EO): 12.0%
8. 1,3-Butylene glycol: 10.0%
9. Purified water: proportion totaling to 100%
10. Antiseptic agent: 0.1%

The cleansing gel prepared according to the above composition had high cleansing function and a moist and vitalizing feel without stickiness, and also excellent stability with time. On the other hand, the cleansing gel blended with the copolymer of Comparative Example 2 in place of the copolymer of Example 8 had a worsened feel due to aggregation of the copolymer, and had insufficient cleansing function and stability with time.

Example 17

Ingredients 1 to 8 listed below are mixed in the respective proportions, and each mixture is heated to 80° C. Further, a mixture prepared by mixing Ingredients 9 to 15 listed below in respective proportions is heated to 80° C. and added to the above mixture while mixing. Subsequently, the mixture was cooled while stirring, to prepare a facial wash foam.
1. Myristic acid: 15.0%
2. Palmitic acid: 5.0%
3. Stearic acid: 3.0%
4. Beeswax: 3.0%
5. POLYETHYLENE GLYCOL 6000: 2.0%
6. Ethylene glycol distearate: 2.0%
7. Coconut oil fatty acid diethanolamide: 3.0%
8. Glycerol: 15.0%
9. (Meth)acrylic acid/alkyl (meth)acrylate ester copolymer (Example 7): 0.1%
10. Sodium hydroxide: 0.04%
11. Potassium hydroxide: 5.5%
12. Sodium pyrrolidonecarboxylate: 0.5%
13. N-Lauroylsarcosine sodium: 10.0%
14. Antiseptic agent: 0.15%
15. Purified water: proportion totaling to 100%

The facial wash foam prepared according to the above composition had a moist and vitalizing feel without stickiness, and also excellent cleansing effect and stability with time. On the other hand, the facial wash foam blended with the copolymer of Comparative Example 3 in place of the copolymer of Example 7 had a worsened feel due to aggregation of the copolymer, and had insufficient stability with time.

Example 18

Ingredients 1 to 10 and Ingredients 11 to 16 listed below are mixed in respective proportions while stirring, and each mixture is heated to 80° C. The latter ingredient mixture is added dropwise to the former ingredient mixture while stirring to emulsify the mixture. Subsequently, the mixture was cooled, to give a sunscreen.
1. (Meth)acrylic acid/alkyl (meth)acrylate ester copolymer (Example 4): 0.1%
2. Carboxymethyl cellulose sodium: 0.3%
3. Sodium hydroxide: 0.28%
4. Ascorbic acid 2-glucoside: 2.0%
5. Citric acid: 0.01%
6. Sodium hydrogenphosphate: 0.1%
7. Antiseptic agent: 0.15%
8. 1,3-Butylene glycol: 7.0%
9. Glycerol: 8.0%
10. Purified water: proportion totaling to 100%
11. Sorbitan monostearate: 0.5%
12. Polyoxyethylene sorbitan monooleate (20EO): 0.5%
13. Sorbitan sesquioleate: 0.5%
14. Cetanol: 2.0%
15. 2-Ethylhexyl paramethoxycinnamate: 10.0%
16. Ethanol: 10.0%

The sunscreen prepared according to the above composition had a moist and vitalizing feel without stickiness, and also excellent stability with time. On the other hand, the sunscreen blended with the copolymer of Comparative Example 4 in place of the copolymer of Example 4 had a worsened feel due to aggregation of the copolymer, and had insufficient stability with time.

Example 19

Ingredients 1 to 7 listed below were dissolved in respective proportions at an ambient temperature and homogeneously mixed while stirring, to prepare a styling gel.
1. Carboxyvinyl polymer*1: 0.1%
   *1: AQUPEC HV-501E, manufactured by Sumitomo Seika Co., Ltd.
2. (Meth)acrylic acid/alkyl (meth)acrylate ester copolymer (Example 5): 0.1%
3. Sodium hydroxide: 0.08%
4. Vinyl pyrrolidone-vinyl acetate copolymer solution (H)*2: 10.0%
   *2: PVP/VAE-735, manufactured by ISP
5. Sodium pyrrolidonecarboxylate: 1.0%
6. Antiseptic agent: 0.1%
7. Purified water: proportion totaling to 100%

The styling gel prepared according to the above composition had a moist and vitalizing feel without stickiness, and also excellent lastingness of makeup and stability with time. On the other hand, the styling gel blended with the copolymer of Comparative Example 5 in place of the copolymer of Example 5 had a worsened feel due to aggregation of the copolymer, and had insufficient lastingness of makeup and stability with time.

Example 20

Ingredients 1 to 9 listed below were dissolved at an ambient temperature in respective proportions and homogeneously mixed while stirring, to prepare an eyeliner.
1. Alkyl acrylate copolymer emulsion*3: 30.0%
  *3: YODOSOL GH810, manufactured by Nippon NSC
2. 1,3-Butylene glycol: 15.0%
3. Black iron oxide: 15.0%
4. (Meth)acrylic acid/alkyl (meth)acrylate ester copolymer (Example 1): 0.1%
5. Sodium hydroxide: 0.04%
6. Carboxymethyl cellulose sodium: 2.0%
7. Sodium chloride: 0.5%
8. Antiseptic agent: 0.15%
9. Purified water: proportion totaling to 100%

The eyeliner prepared according to the above composition had a moist and vitalizing feel without stickiness, and also excellent lastingness of makeup and stability with time. On the other hand, the eyeliner blended with the copolymer of Comparative Example 6 in place of the copolymer of Example 1 had a worsened feel due to aggregation of the copolymer, and had insufficient lastingness of makeup and stability with time.

Example 21

Ingredients 1 to 10 and Ingredients 11 to 16 listed below are mixed in respective proportions while stirring, and each mixture is heated to 80° C. The latter ingredient mixture is added dropwise to the former ingredient mixture while stirring to emulsify the mixture. Subsequently, the mixture was cooled, to give a mascara.
1. Stearic acid: 2.0%
2. Carnauba wax: 2.0%
3. Beeswax: 3.0%
4. Polyoxyethylene sorbitan monooleate (20EO): 1.0%
5. Sorbitan sesquioleate: 0.5%
6. Alkyl acrylate copolymer emulsion*3: 1.0%
  *3: YODOSOL GH810, manufactured by Nippon NSC
7. Triethanolamine: 1.1%
8. Propylene glycol: 1.0%
9. Black iron oxide: 10.0%
10. Kaolin: 10.0%
11. (Meth)acrylic acid/alkyl (meth)acrylate ester copolymer (Example 2): 0.2%
12. Sodium hydroxide: 0.08%
13. Carboxymethyl cellulose sodium: 2.5%
14. Sodium chloride: 0.1%
15. Antiseptic agent: 0.15%
16. Purified water: proportion totaling to 100%

The mascara prepared according to the above composition had smooth spreadability, and also excellent lastingness of makeup and stability with time. On the other hand, the mascara blended with the copolymer of Comparative Example 2 in place of the copolymer of Example 2 had a worsened feel due to aggregation of the copolymer, and had insufficient lastingness of makeup and stability with time.

Example 22

Ingredients 1 to 11 listed below are added in respective proportions, and dispersed by a roller treatment. The dispersion is injected into a mold at a high temperature and cooled. The molded product was filled into a vessel to prepare a lipstick.
1. Candelilla wax: 5.0%
2. Ceresin: 5.0%
3. Carnauba wax: 3.0%
4. Microcrystalline wax: 3.0%
5. Glycerol tri-2-ethylhexanoate: 20.0%
6. Isotridecyl isononanoate: 20.0%
7. Diisostearyl malate: proportion totaling to 100%
8. (Meth)acrylic acid/alkyl (meth)acrylate ester copolymer (Example 3): 1.0%
9. Silicic acid anhydride: 1.0%
10. Coloring agent: 20.0%
11. Antiseptic agent: 0.1%

The lipstick prepared according to the above composition had a smooth feel upon use, and also excellent lastingness of makeup and stability with time. On the other hand, the lipstick blended with the copolymer of Comparative Example 3 in place of the copolymer of Example 3 had a worsened feel due to aggregation of the copolymer, and had insufficient lastingness of makeup and stability with time.

Example 23

Ingredients 1 to 11 listed below are mixed in respective proportions, and each mixture is heated to 80° C. Further, a mixture prepared by mixing Ingredients 12 to 18 listed below in respective proportions is heated to 80° C. and added to the above mixture while mixing. Subsequently, the mixture was cooled while stirring, to prepare a foundation.
1. Lipophilic glycerol monostearate: 1.0%
2. Stearic acid: 5.0%
3. Behenyl alcohol: 1.0%
4. Cetanol: 0.5%
5. Squalane: 5.0%
6. Titanium oxide: 4.0%
7. Red iron oxide: 0.5%
8. Yellow iron oxide: 1.0%
9. Black iron oxide: 0.03%
10. Talc: 4.0%
11. Soybean phospholipid: 0.3%
12. 1,3-Butylene glycol: 8.0%
13. Triethanolamine: 1.5%
14. (Meth)acrylic acid/alkyl (meth)acrylate ester copolymer (Example 6): 0.2%
15. Sodium hydroxide: 0.08%
16. Sodium pyrrolidonecarboxylate: 1.0%
17. Antiseptic agent: 0.1%
18. Purified water: proportion totaling to 100%

The foundation prepared according to the above composition had smooth spreadability and a moist and vitalizing feel without stickiness, and also excellent lastingness of makeup. Also, the foundation had excellent stability with time. On the other hand, the foundation blended with the copolymer of Comparative Example 6 in place of the copolymer of Example 6 had poorer spreadability, lacked a moist and vitalizing feel, and had poor lastingness of makeup. Further, it had poor stability with time.

Example 24

Ingredients 1 to 5 listed below in respective proportions were mixed, and the mixture was stirred until it was homogenous, Ingredients 6 to 9 were further added thereto, and the resulting mixture was homogeneously mixed, to produce a gel-like state, to prepare a cleansing gel.

1. (Meth)acrylic acid/alkyl (meth)acrylate ester copolymer (Example 7): 1.0%
2. Purified water: proportion totaling to 100%
3. Potassium hydroxide: 0.25%
4. Sodium chloride: 0.5%
5. Lactic acid: 0.01%
6. Antiseptic agent: 0.15%
7. Ethanol: 8.0%
8. 1,3-Butylene glycol: 5.0%
9. Lauroylmethylalanine sodium: 5.0%

The cleansing gel prepared according to the above composition had a moist and vitalizing feel without stickiness, and also excellent cleansing effect and stability with time. On the other hand, the cleansing gel blended with the copolymer of Comparative Example 3 in place of the copolymer of Example 7 had a worsened feel due to aggregation of the copolymer, and had insufficient cleansing effect and stability with time.

Example 25

Ingredients 1 to 6 listed below were mixed in respective proportions, while stirring until the mixture was homogenous, Ingredients 7 to 12 were further added thereto, and the resulting mixture was homogeneously mixed, to produce a gel-like state, to prepare a cleansing gel.
1. (Meth)acrylic acid/alkyl (meth)acrylate ester copolymer (Example 7): 0.2%
2. Purified water: 10.0%
3. Triethanolamine: 0.2%
4. Sodium chloride: 0.2%
5. Sodium lactate: 0.01%
6. Hydroxypropylmethyl cellulose: 5.0%
7. Purified water: proportion totaling to 100%
8. Polyoxyethylene cetyl ether (30EO): 16.0%
9. Polyoxyethylene lauryl ether (5EO): 12.0%
10. 1,2-Pentanediol: 5.0%
11. Phenoxyethanol: 0.5%
12. Antiseptic agent: 0.1%

The cleansing gel prepared according to the above composition had a moist and vitalizing feel without stickiness, and also excellent cleansing effect and stability with time. On the other hand, the cleansing gel blended with the copolymer of Comparative Example 5 in place of the copolymer of Example 7 had a worsened feel due to aggregation of the copolymer, and had insufficient cleansing effect and stability with time.

Example 26

Ingredients 1 to 4 listed below in respective proportions were mixed and the mixture was stirred until it was homogenous, a mixture prepared by previously mixing Ingredients 5 to 11 was further added thereto, and the resulting mixture was stirred until the mixture had a homogeneous gel-like state, to prepare a cleansing gel.
1. Decamethyl cyclopentasiloxane: 20.0%
2. Dimethyl poly(siloxane)*4: 1.0%
3. Liquid paraffin: 5.0%
4. Polyoxyethylene isostearic acid (10EO): 5.0%
5. (Meth)acrylic acid/alkyl (meth)acrylate ester copolymer (Example 7): 1.0%
6. Sodium hydroxide: 0.3%
7. Sodium chloride: 0.7%
8. L-Serine: 0.5%
9. Hydroxyethyl cellulose: 0.02%
10. Antiseptic agent: 0.15%
11. Purified water: proportion totaling to 100%

*4: Silicone KF-96 (100 Cs), manufactured by Shin-Etsu Chemical Co., Ltd.

The cleansing gel prepared according to the above composition had a moist and vitalizing feel without stickiness, and also excellent cleansing effect and stability with time. On the other hand, the cleansing gel blended with the copolymer of Comparative Example 6 in place of the copolymer of Example 7 had a worsened feel due to aggregation of the copolymer, and had insufficient cleansing effect and stability with time.

Example 27

Ingredients 1 to 3 listed below in respective proportions were mixed, the mixture was stirred until it was homogenous, a mixture prepared by previously mixing Ingredients 4 to 9 was further added thereto, and the resulting mixture was stirred until the mixture had a homogeneous gel-like state, to prepare a cleansing gel.
1. Glycerol tri(caprylate-caprate): 20.0%
2. Polyoxyethylene sorbitan monooleate (6EO): 20.0%
3. Glycerol: 30.0%
4. (Meth)acrylic acid/alkyl (meth)acrylate ester copolymer (Example 7): 2.0%
5. Sodium hydroxide: 0.6%
6. Sodium chloride: 2.0%
7. Arbutin: 0.5%
8. Antiseptic agent: 0.1%
9. Purified water: proportion totaling to 100%

The cleansing gel prepared according to the above composition had a moist and vitalizing feel without stickiness, and also excellent cleansing effect and stability with time. On the other hand, the cleansing gel blended with the copolymer of Comparative Example 4 in place of the copolymer of Example 7 had a worsened feel due to aggregation of the copolymer, and had insufficient cleansing effect and stability with time.

Example 28

Ingredients 1 to 8 listed below are mixed in respective proportions and heated to 80° C. Further, Ingredients 9 and 10 are added thereto, and the resulting mixture is stirred until it is homogenous. A mixture prepared by previously homogeneously mixing Ingredients 11 to 15 was further added thereto and cooled to 30° C. while stirring, to prepare a facial wash foam.
1. Myristic acid: 15.0%
2. Palmitic acid: 5.0%
3. Stearic acid: 3.0%
4. Glycerol stearate: 3.0%
5. Ethylene glycol distearate: 2.0%
6. Coconut oil fatty acid diethanolamide: 3.0%
7. Glycerol: 15.0%
8. Antiseptic agent: 0.15%
9. Potassium hydroxide: 5.5%
10. Purified water: 14.5%
11. (Meth)acrylic acid/alkyl (meth)acrylate ester copolymer (Example 3): 0.1%
12. Potassium chloride: 0.05%
13. Citric acid: 0.04%
14. Sodium citrate: 0.01%
15. Purified water: proportion totaling to 100%

The facial wash foam prepared according to the above composition had a moist and vitalizing feel without stickiness, and also excellent cleansing effect and stability with time. On the other hand, the facial wash foam blended with the copolymer of Comparative Example 2 in place of the copolymer of Example 3 had a worsened feel due to aggregation of the copolymer, and had insufficient cleansing effect and stability with time.

Example 29

Ingredients 1 to 10 listed below are mixed in respective proportions and heated to 80° C. Further, Ingredients 11 and 12 are added thereto, and the mixture is stirred until it is homogenous. A mixture prepared by previously homogeneously mixing Ingredients 13 to 16 was further added thereto, and the resulting mixture was cooled to 30° C. while stirring, to prepare a facial wash foam.
1. Lauric acid: 2.0%
2. Myristic acid: 20.0%
3. Palmitic acid: 5.0%
4. Stearic acid: 5.0%
5. Coconut oil fatty acid potassium: 8.0%
6. Coconut oil fatty acid diethanolamide: 3.0%
7. Sodium coconut acid methyl taurate: 4.0%
8. Glycerol: 10.0%
9. 1,3-Butylene glycol: 10.0%
10. Antiseptic agent: 0.1%
11. Potassium hydroxide: 6.0%
12. Purified water: 14.0%
13. (Meth)acrylic acid/alkyl (meth)acrylate ester copolymer (Example 2): 0.2%
14. Potassium chloride: 0.1%
15. Lactic acid: 0.01%
16. Purified water: proportion totaling to 100%

The facial wash foam prepared according to the above composition had a moist and vitalizing feel without stickiness, and also excellent cleansing effect and stability with time. On the other hand, the facial wash foam blended with the copolymer of Comparative Example 1 in place of the copolymer of Example 2 had a worsened feel due to aggregation of the copolymer, and had insufficient cleansing effect and stability with time.

Example 30

Ingredients 1 to 10 listed below are mixed in respective proportions and heated to 80° C. Further, Ingredients 11 and 12 are added thereto, and the mixture is stirred until it is homogenous. A mixture prepared by previously homogeneously mixing Ingredients 13 to 16 was further added thereto, and the resulting mixture was cooled to 30° C. while stirring, to prepare a facial wash foam.
1. Lauric acid: 2.0%
2. Myristic acid: 20.0%
3. Palmitic acid: 5.0%
4. Stearic acid: 5.0%
5. Coconut oil fatty acid potassium: 8.0%
6. Coconut oil fatty acid diethanolamide: 3.0%
7. Sodium coconut acid methyl taurate: 4.0%
8. Glycerol: 10.0%
9. 1,2-Pentanediol: 5.0%
10. Antiseptic agent: 0.15%
11. Potassium hydroxide: 6.0%
12. Purified water: 14.0%
13. (Meth)acrylic acid/alkyl (meth)acrylate ester copolymer (Example 3): 0.2%
14. Potassium chloride: 0.1%
15. Malic acid: 0.01%
16. Purified water: proportion totaling to 100%

The facial wash foam prepared according to the above composition had a moist and vitalizing feel without stickiness, and also excellent cleansing effect and stability with time. On the other hand, the facial wash foam blended with the copolymer of Comparative Example 5 in place of the copolymer of Example 3 had a worsened feel due to aggregation of the copolymer, and had insufficient cleansing effect and stability with time.

Example 31

Ingredients 1 and 2 listed below are mixed in respective proportions and heated to 80° C. Further, a mixture prepared by homogeneously mixing Ingredients 3 to 10 is added thereto, and the mixture is stirred. Subsequently, the mixture was cooled to 30° C. while stirring, to prepare a facial wash foam.
1. Sodium N-lauroylglutamate: 10.0%
2. Polyoxyethylene lauryl ether (20EO): 2.0%
3. Ascorbic acid glucoside: 2.0%
4. (Meth)acrylic acid/alkyl (meth)acrylate ester copolymer (Example 3): 1.0%
5. Sodium hydroxide: 0.3%
6. Sodium chloride: 0.5%
7. Malic acid: 0.03%
8. Collagen: 0.5%
9. Antiseptic agent: 0.1%
10. Purified water: proportion totaling to 100%

The facial wash foam prepared according to the above composition had a moist and vitalizing feel without stickiness, and also excellent cleansing effect and stability with time. On the other hand, the facial wash foam blended with the copolymer of Comparative Example 2 in place of the copolymer of Example 3 had a worsened feel due to aggregation of the copolymer, and had insufficient cleansing effect and stability with time.

Example 32

Ingredients 1 to 4 listed below are mixed in respective proportions and heated to 80° C. Further, a mixture prepared by homogeneously mixing Ingredients 5 to 10 is added thereto, and the mixture is stirred. Subsequently, the mixture was cooled to 30° C. while stirring, to prepare a facial wash foam.
1. Decaglycerol monolaurate: 30.0%
2. 1,3-Butylene glycol: 15.0%
3. Decyl glucoside: 2.5%
4. Antiseptic agent: 0.15%
5. (Meth)acrylic acid/alkyl (meth)acrylate ester copolymer (Example 5): 2.0%
6. Sodium hydroxide: 0.6%
7. Sodium chloride: 1.0%
8. Sodium pyrrolidonecarboxylate: 0.03%
9. Dipotassium glycyrrhizate: 0.1%
10. Purified water: proportion totaling to 100%

The facial wash foam prepared according to the above composition had a moist and vitalizing feel without stickiness, and also excellent cleansing effect and stability with time. On the other hand, the facial wash foam blended with the copolymer of Comparative Example 4 in place of the copolymer of Example 5 had a worsened feel due to aggregation of the copolymer, and had insufficient cleansing effect and stability with time.

Example 33

Ingredients 1 to 6 listed below are mixed in respective proportions and heated to 70° C. Further, a mixture prepared by mixing Ingredients 7 to 12 is gradually added thereto, and the mixture is stirred until it is homogeneous. Subsequently, the mixture was cooled to 30° C. while stirring, to prepare a clear shampoo.
1. Sodium coconut acid methyl taurate: 4.0%
2. Sodium polyoxyethylene lauryl ether sulfate (12EO): 8.0%
3. Lauryldimethylaminoacetate betaine: 4.0%
4. Sodium cocoamphoacetate: 3.0%
5. Coconut oil fatty acid diethanolamide: 5.0%
6. Antiseptic agent: 0.1%
7. Citric acid: 0.1%
8. 1,2-Pentanediol: 5.0%
9. (Meth)acrylic acid/alkyl (meth)acrylate ester copolymer (Example 2): 0.5%
10. Sodium chloride: 0.5%
11. Proline: 0.05%
12. Purified water: proportion totaling to 100%

The clear shampoo prepared according to the above composition had a moist and vitalizing feel without stickiness, and also excellent stability with time. On the other hand, the clear shampoo blended with the copolymer of Comparative Example 3 in place of the copolymer of Example 2 had a worsened feel due to aggregation of the copolymer, and had insufficient stability with time.

Example 34

Ingredients 1 to 10 listed below are mixed in respective proportions and heated to 80° C. Further, a mixture prepared by previously homogeneously mixing Ingredients 11 to 16 is gradually added thereto, and the mixture is stirred until it is homogeneous. Subsequently, the mixture was cooled to 30° C. while stirring, to prepare a pearly shampoo.
1. Sodium polyoxyethylene lauryl ether sulfate (8EO): 12.0%
2. Ammonium polyoxyethylene lauryl ether sulfate (3EO): 10.0%
3. Lauryldimethylaminoacetate betaine: 2.0%
4. POLYQUATERNIUM-39 (9.9% aqueous solution): 1.0%
5. O-[2-Hydroxy-3-(trimethylammonio)propyl]hydroxyethyl cellulose chloride: 0.3%
6. Coconut oil fatty acid diethanolamide: 5.0%
7. Ethylene glycol distearate: 2.0%
8. Polymeric methyl poly(siloxane) emulsion*5: 0.5%
  *5: BY22-020, manufactured by Dow Corning Toray Co., Ltd.
9. 1,3-Butylene glycol: 3.0%
10. Antiseptic agent: 0.15%
11. (Meth)acrylic acid/alkyl (meth)acrylate ester copolymer (Example 3): 0.5%
12. Sodium chloride: 0.5%
13. Glycine: 0.01%
14. Malic acid: 0.1%
15. Arginine: 0.01%
16. Purified water: proportion totaling to 100%

The pearly shampoo prepared according to the above composition had a moist and vitalizing feel without stickiness, and also excellent stability with time. On the other hand, the pearly shampoo blended with the copolymer of Comparative Example 5 in place of the copolymer of Example 3 had a worsened feel due to aggregation of the copolymer, and had insufficient stability with time.

Example 35

Ingredients 1 to 5 listed below are mixed in respective proportions and heated to 80° C. Further, a mixture prepared by previously homogeneously mixing Ingredients 6 to 9 is gradually added thereto, and the mixture is stirred until it is homogeneous. Subsequently, the mixture was cooled to 30° C. while stirring, to prepare a body shampoo.
1. Cocoyl glutamate triethanolamine: 12.0%
2. Sodium polyoxyethylene tridecyl ether acetate (3EO): 10.0%
3. POLYQUATERNIUM-39 (9.9% aqueous solution): 3.0%
4. 1,3-Butylene glycol: 5.0%
5. Antiseptic agent: 0.1%
6. (Meth)acrylic acid/alkyl (meth)acrylate ester copolymer (Example 4): 0.25%
7. Sodium chloride: 0.1%
8. Glutamic acid: 0.02%
9. Purified water: proportion totaling to 100%

The body shampoo prepared according to the above composition had a moist and vitalizing feel without stickiness, and also excellent stability with time. On the other hand, the body shampoo blended with the copolymer of Comparative Example 1 in place of the copolymer of Example 4 had a worsened feel due to aggregation of the copolymer, and had insufficient stability with time.

Example 36

Ingredients 1 to 6 listed below are mixed in respective proportions and heated to 80° C. Further, a mixture prepared by previously homogeneously mixing Ingredients 7 to 10 is gradually added thereto, and the mixture is stirred until it is homogeneous. Subsequently, the mixture was cooled to 30° C. while stirring, to prepare a body shampoo.
1. Lauroylmethylalanine sodium: 13.0%
2. Sodium cocoamphoacetate: 5.0%
3. Coconut oil fatty acid potassium: 10.0%
4. Coconut oil fatty acid diethanolamide: 5.0%
5. Ethylene glycol distearate: 2.0%
6. Antiseptic agent: 0.15%
7. (Meth)acrylic acid/alkyl (meth)acrylate ester copolymer (Example 5): 0.25%
8. Sodium chloride: 0.1%
9. N-Acetyl-L-glutamic acid: 0.02%
10. Purified water: proportion totaling to 100%

The body shampoo prepared according to the above composition had a moist and vitalizing feel without stickiness, and also excellent stability with time. On the other hand, the body shampoo blended with the copolymer of Comparative Example 6 in place of the copolymer of Example 5 had a worsened feel due to aggregation of the copolymer, and had insufficient stability with time.

Example 37

Ingredients 1 to 3 listed below are mixed in respective proportions and heated to 80° C. Further, a mixture prepared by previously homogeneously mixing Ingredients 4 to 13 is gradually added thereto, and the mixture is stirred until it is homogeneous. Subsequently, the mixture was cooled to 30° C. while stirring, to prepare a body shampoo.
1. Triethanolamine myristate: 10.0%
2. Potassium laurate: 15.0%
3. Aminoethylaminopropyl siloxane-dimethyl siloxane copolymer: 2.0%
4. Bentonite: 1.0%
5. Glycerol: 5.0%
6. Propylene glycol: 5.0%
7. Hydroxyethyl cellulose: 0.3%
8. (Meth)acrylic acid/alkyl (meth)acrylate ester copolymer (Example 1): 0.3%
9. Sodium hydroxide: 0.1%

10. Sodium chloride: 0.4%
11. Glycine: 0.5%
12. Antiseptic agent: 0.1%
13. Purified water: proportion totaling to 100%

The body shampoo prepared according to the above composition had a moist and vitalizing feel without stickiness, and also excellent stability with time. On the other hand, the body shampoo blended with the copolymer of Comparative Example 4 in place of the copolymer of Example 1 had a worsened feel due to aggregation of the copolymer, and had insufficient stability with time.

Example 38

Ingredients 1 to 3 listed below are mixed in respective proportions, the mixture is stirred until it is homogeneous, Ingredient 4 is added thereto, Ingredient 5 is then added thereto while stirring, and the mixture is heated to 40° C. Further, Ingredient 6 was added thereto, and the mixture was stirred to produce a gel-like state, to prepare a hair-setting gel.
1. Purified water: proportion totaling to 100%
2. Glycerol: 4.0%
3. Antiseptic agent: 0.15%
4. (Meth)acrylic acid/alkyl (meth)acrylate ester copolymer (Example 6): 1.0%
5. Sodium hydroxide: 0.4%
6. POLYQUATERNIUM 11(50% ethanol solution): 6.0%

The hair-setting gel prepared according to the above composition had a moist and vitalizing feel without stickiness, and also excellent lastingness of makeup and stability with time. On the other hand, the hair-setting gel blended with the copolymer of Comparative Example 6 in place of the copolymer of Example 6 had a worsened feel due to aggregation of the copolymer, and had insufficient lastingness of makeup and stability with time.

The cosmetics in which the (meth)acrylic acid/alkyl (meth) acrylate ester copolymers obtained in Examples 1 to 8 mentioned above were used had a moist and vitalizing feel without stickiness. Further, even the cosmetics blended with an electrolyte or the like had similar properties.

INDUSTRIAL APPLICABILITY

Since the (meth)acrylic acid/alkyl (meth)acrylate ester copolymer of the present invention can be utilized as a thickener having excellent properties, various cosmetics having a moist and vitalizing feel without stickiness, such as lotion, emulsion, essence, cream, cream pack, massage cream, cleansing cream, cleansing gel, facial wash foam, sunscreen, styling gel, eyeliner, mascara, lipstick, foundation, clear shampoo, pearly shampoo, body shampoo and hair-setting gel can be provided.

The invention claimed is:
1. A (meth)acrylic acid/alkyl (meth)acrylate ester copolymer comprising:
   95.42 to 97.48% by mass of (meth)acrylic acid;
   2.43 to 4.30% by mass of an alkyl (meth)acrylate ester, which is at least one selected from the group consisting of eicosanyl (meth)acrylate, behenyl (meth)acrylate, and tetracosanyl (meth)acrylate,
   or a mixture of two to four members selected from the group consisting of stearyl (meth)acrylate, eicosanyl (meth)acrylate, behenyl (meth)acrylate, and tetracosanyl (meth)acrylate; and
   0.08 to 0.30% by mass of a compound having two or more ethylenically unsaturated groups,
   wherein the (meth)acrylic acid/alkyl (meth)acrylate ester copolymer has the following properties:
   1) a viscosity of a neutral viscous aqueous solution comprising 1% by mass of the (meth)acrylic acid/alkyl (meth)acrylate ester copolymer and 1% by mass of sodium chloride of 40000 mPa·s or more at 25° C., and a ratio of a viscosity of the neutral viscous aqueous solution at 25° C. to a viscosity of the neutral viscous aqueous solution at 50° C. of from 1:0.8 to 1:1.2; and
   2) a ratio of a viscosity of a neutral viscous aqueous solution comprising 1% by mass of the (meth)acrylic acid/alkyl (meth)acrylate ester copolymer and 1% by mass of sodium chloride at 25° C. to a viscosity of a neutral viscous aqueous solution containing 1% by mass of the (meth)acrylic acid/alkyl (meth)acrylate ester copolymer and 0.5% by mass of sodium chloride at 25° C. of from 1:0.75 to 1:1.25.
2. The (meth)acrylic acid/alkyl (meth)acrylate ester copolymer according to claim 1, wherein the alkyl (meth)acrylate ester is at least one selected from the group consisting of eicosanyl (meth)acrylate, behenyl (meth)acrylate, and tetracosanyl (meth)acrylate.
3. The (meth)acrylic acid/alkyl (meth)acrylate ester copolymer according to claim 1, wherein the compound having two or more ethylenically unsaturated groups is at least one selected from the group consisting of pentaerythritol diallyl ether, pentaerythritol triallyl ether, pentaerythritol tetraallyl ether, diethylene glycol diallyl ether, polyethylene glycol diallyl ether, and polyallyl saccharose.
4. A cosmetic comprising the (meth)acrylic acid/alkyl (meth)acrylate ester copolymer as defined claim 1.
5. The cosmetic according to claim 4, wherein the cosmetic further comprises an electrolyte.
6. A thickener comprising the (meth)acrylic acid/alkyl (meth)acrylate ester copolymer as defined in claim 1.
7. The (meth)acrylic acid/alkyl (meth)acrylate ester copolymer according to claim 1, wherein the alkyl (meth)acrylate ester is a mixture of two to four members selected from the group consisting of stearyl (meth)acrylate, eicosanyl (meth)acrylate, behenyl (meth)acrylate, and tetracosanyl (meth)acrylate.
8. The (meth)acrylic acid/alkyl (meth)acrylate ester copolymer according to claim 1, comprising:
   95.47 to 97.46% by mass of (meth)acrylic acid;
   2.91 to 3.84% by mass of said alkyl (meth)acrylate ester; and
   0.11 to 0.24% by mass of said compound having two or more ethylenically unsaturated groups.
9. The (meth)acrylic acid/alkyl (meth)acrylate ester copolymer according to claim 1, comprising:
   95.97 to 96.94% by mass of (meth)acrylic acid;
   2.91 to 3.84% by mass of said alkyl (meth)acrylate ester; and
   0.15 to 0.19% by mass of said compound having two or more ethylenically unsaturated groups.
10. The (meth)acrylic acid/alkyl (meth)acrylate ester copolymer according to claim 1, wherein the (meth)acrylic acid/alkyl (meth)acrylate ester copolymer has the following properties:
   1) a viscosity of a neutral viscous aqueous solution comprising 1% by mass of the (meth)acrylic acid/alkyl (meth)acrylate ester copolymer and 1% by mass of sodium chloride of 42000 mPa·s or more at 25° C., and a ratio of a viscosity of the neutral viscous aqueous solution at 25° C. to a viscosity of the neutral viscous aqueous solution at 50° C. of from 1:0.9 to 1:1.1; and

2) a ratio of a viscosity of a neutral viscous aqueous solution comprising 1% by mass of the (meth)acrylic acid/alkyl (meth)acrylate ester copolymer and 1% by mass of sodium chloride at 25° C. to a viscosity of a neutral viscous aqueous solution containing 1% by mass of the (meth)acrylic acid/alkyl (meth)acrylate ester copolymer and 0.5% by mass of sodium chloride at 25° C. of from 1:0.90 to 1:20.

11. The (meth)acrylic acid/alkyl (meth)acrylate ester copolymer according to claim 8, wherein the (meth)acrylic acid/alkyl (meth)acrylate ester copolymer has the following properties:
  1) a viscosity of a neutral viscous aqueous solution comprising 1% by mass of the (meth)acrylic acid/alkyl (meth)acrylate ester copolymer and 1% by mass of sodium chloride of 42000 mPa·s or more at 25° C., and a ratio of a viscosity of the neutral viscous aqueous solution at 25° C. to a viscosity of the neutral viscous aqueous solution at 50° C. of from 1:0.9 to 1:1.1; and
  2) a ratio of a viscosity of a neutral viscous aqueous solution comprising 1% by mass of the (meth)acrylic acid/alkyl (meth)acrylate ester copolymer and 1% by mass of sodium chloride at 25° C. to a viscosity of a neutral viscous aqueous solution containing 1% by mass of the (meth)acrylic acid/alkyl (meth)acrylate ester copolymer and 0.5% by mass of sodium chloride at 25° C. of from 1:0.90 to 1:20.

12. The (meth)acrylic acid/alkyl (meth)acrylate ester copolymer according to claim 9, wherein the (meth)acrylic acid/alkyl (meth)acrylate ester copolymer has the following properties:
  1) a viscosity of a neutral viscous aqueous solution comprising 1% by mass of the (meth)acrylic acid/alkyl (meth)acrylate ester copolymer and 1% by mass of sodium chloride of 42000 mPa·s or more at 25° C., and a ratio of a viscosity of the neutral viscous aqueous solution at 25° C. to a viscosity of the neutral viscous aqueous solution at 50° C. of from 1:0.9 to 1:1.1; and
  2) a ratio of a viscosity of a neutral viscous aqueous solution comprising 1% by mass of the (meth)acrylic acid/alkyl (meth)acrylate ester copolymer and 1% by mass of sodium chloride at 25° C. to a viscosity of a neutral viscous aqueous solution containing 1% by mass of the (meth)acrylic acid/alkyl (meth)acrylate ester copolymer and 0.5% by mass of sodium chloride at 25° C. of from 1:0.90 to 1:20.

13. The (meth)acrylic acid/alkyl (meth)acrylate ester copolymer according to claim 1, comprising:
  95.47 to 97.46% by mass of acrylic acid;
  2.91 to 3.84% by mass of said alkyl (meth)acrylate ester; and
  0.11 to 0.24% by mass of at least one selected from the group consisting of pentaerythritol diallyl ether, pentaerythritol triallyl ether, and pentaerythritol tetraallyl ether.

14. The (meth)acrylic acid/alkyl (meth)acrylate ester copolymer according to claim 1, comprising:
  95.97 to 96.94% by mass of acrylic acid;
  2.91 to 3.84% by mass of said alkyl (meth)acrylate ester; and
  0.15 to 0.19% by mass of at least one selected from the group consisting of pentaerythritol diallyl ether, pentaerythritol triallyl ether, and pentaerythritol tetraallyl ether.

15. The (meth)acrylic acid/alkyl (meth)acrylate ester copolymer according to claim 2, wherein the compound having two or more ethylenically unsaturated groups is at least one selected from the group consisting of pentaerythritol diallyl ether, pentaerythritol triallyl ether, pentaerythritol tetraallyl ether, diethylene glycol diallyl ether, polyethylene glycol diallyl ether, and polyallyl saccharose.

16. The (meth)acrylic acid/alkyl (meth)acrylate ester copolymer according to claim 7, wherein the compound having two or more ethylenically unsaturated groups is at least one selected from the group consisting of pentaerythritol diallyl ether, pentaerythritol triallyl ether, pentaerythritol tetraallyl ether, diethylene glycol diallyl ether, polyethylene glycol diallyl ether, and polyallyl saccharose.

17. The (meth)acrylic acid/alkyl (meth)acrylate ester copolymer according to claim 8, wherein the compound having two or more ethylenically unsaturated groups is at least one selected from the group consisting of pentaerythritol diallyl ether, pentaerythritol triallyl ether, pentaerythritol tetraallyl ether, diethylene glycol diallyl ether, polyethylene glycol diallyl ether, and polyallyl saccharose.

18. The (meth)acrylic acid/alkyl (meth)acrylate ester copolymer according to claim 9, wherein the compound having two or more ethylenically unsaturated groups is at least one selected from the group consisting of pentaerythritol diallyl ether, pentaerythritol triallyl ether, pentaerythritol tetraallyl ether, diethylene glycol diallyl ether, polyethylene glycol diallyl ether, and polyallyl saccharose.

19. The (meth)acrylic acid/alkyl (meth)acrylate ester copolymer according to claim 10, wherein the compound having two or more ethylenically unsaturated groups is at least one selected from the group consisting of pentaerythritol diallyl ether, pentaerythritol triallyl ether, pentaerythritol tetraallyl ether, diethylene glycol diallyl ether, polyethylene glycol diallyl ether, and polyallyl saccharose.

20. The (meth)acrylic acid/alkyl (meth)acrylate ester copolymer according to claim 11, wherein the compound having two or more ethylenically unsaturated groups is at least one selected from the group consisting of pentaerythritol diallyl ether, pentaerythritol triallyl ether, pentaerythritol tetraallyl ether, diethylene glycol diallyl ether, polyethylene glycol diallyl ether, and polyallyl saccharose.

* * * * *